(12) United States Patent
Allstrom

(10) Patent No.: US 12,345,730 B2
(45) Date of Patent: Jul. 1, 2025

(54) DIFFERENTIAL DENSITY SYSTEM AND METHOD

(71) Applicant: Schneider Electric Systems, USA Inc., Foxborough, MA (US)

(72) Inventor: Peter Allstrom, Warwick, RI (US)

(73) Assignee: SCHNEIDER ELECTRIC SYSTEMS USA, INC., Foxboro, MA (US)

( * ) Notice: Subject to any disclaimer, the term of this patent is extended or adjusted under 35 U.S.C. 154(b) by 301 days.

(21) Appl. No.: 18/145,110

(22) Filed: Dec. 22, 2022

(65) Prior Publication Data

US 2023/0304908 A1    Sep. 28, 2023

Related U.S. Application Data

(60) Provisional application No. 63/322,826, filed on Mar. 23, 2022.

(51) Int. Cl.
| | |
|---|---|
| *G01N 9/36* | (2006.01) |
| *G01L 7/08* | (2006.01) |
| *G01L 13/02* | (2006.01) |
| *G01L 19/04* | (2006.01) |
| *G01L 27/00* | (2006.01) |
| *G01N 9/26* | (2006.01) |
| *G01L 19/00* | (2006.01) |

(52) U.S. Cl.
CPC .......... *G01N 9/36* (2013.01); *G01L 7/082* (2013.01); *G01L 13/025* (2013.01); *G01L 19/04* (2013.01); *G01L 27/002* (2013.01); *G01N 9/26* (2013.01); *G01L 2019/0053* (2013.01)

(58) Field of Classification Search
CPC . G01N 9/36; G01N 9/26; G01N 33/18; G01L 7/082; G01L 13/025; G01L 19/04; G01L 27/002; G01L 2019/0053; G01L 13/026; C02F 1/441; C02F 2103/08; C02F 2209/02; C02F 2209/03; C02F 2209/05
USPC ..... 73/1.01, 1.57, 1.59, 1.63, 32 R, 716–722
See application file for complete search history.

(56) References Cited

U.S. PATENT DOCUMENTS

| | | |
|---|---|---|
| 3,771,348 A | 11/1973 | Villarroel |
| 4,175,426 A | 11/1979 | Rosenblum |
| 4,328,699 A | 5/1982 | Drzewiecki |

FOREIGN PATENT DOCUMENTS

RU    2348918 C2 *  3/2009

OTHER PUBLICATIONS

International Search Report and Written Opinion from PCT Application No. PCT/US2023/015391, dated Jul. 21, 2023, 11 pages.

* cited by examiner

*Primary Examiner* — Robert R Raevis
(74) *Attorney, Agent, or Firm* — Stinson LLP

(57) ABSTRACT

Differential density system and method. A differential pressure transmitter measures a pressure difference between first and second pressure sensing locations. A reference vessel in fluid communication with the first pressure sensing location contains a reference fluid and a sample vessel in fluid communication with the second pressure sensing location contains a sample fluid. The reference fluid is in a first column above the first pressure sensing location and the sample fluid is in a second column above the second pressure sensing location. The second column is of substantially equal height as the first column. A value of total dissolved solids (TDS) in the sample fluid is determined based on the pressure difference.

19 Claims, 6 Drawing Sheets

DIFFERENTIAL DENSITY SYSTEM AND METHOD

CROSS-REFERENCE TO RELATED APPLICATION

This application claims priority to U.S. Provisional Patent Application No. 63/322,826, filed Mar. 23, 2022, the entire disclosure of which is incorporated herein by reference.

BACKGROUND

Desalination plants, for instance, are interested in measuring total dissolved solids (TDS) at different points of the process. This measurement is typically determined by using a conductivity meter. The conductivity measurement is temperature dependent and even though it is temperature-compensated to a reference temperature value, such meters can be inaccurate and inconsistent with respect to the desired performance. Conventional TDS estimates calculated from conductivity measurements meters provide low accuracy (e.g., 5% error). More accurate and highly repeatable TDS measurements are needed.

SUMMARY

Aspects of the present disclosure use a specific measurement configuration in combination with a differential pressure (DP) transmitter for measuring density to calculate TDS. Differential density measurements in accordance with aspects of the present disclosure provide an accurate value for TDS with minimal temperature affects. This results in a more repeatable TDS value over a desired operating range. Advantageously, aspects of the present disclosure minimize temperature error on the TDS calculation and provide improved accuracy and repeatability over conventional conductivity-based TDS measurements.

In an aspect, a differential density system comprises a differential pressure transmitter having first and second pressure sensing locations, a reference vessel in fluid communication with the first pressure sensing location, and a sample vessel in fluid communication with the second pressure sensing location. The reference vessel is configured to contain a reference fluid in a first column above the first pressure sensing location and the sample vessel is configured to contain a sample fluid in a second column above the second pressure sensing location. The second column is of substantially equal height as the first column. The differential pressure transmitter is configured to measure a pressure difference between the first and second pressure sensing locations when the reference fluid is in the reference vessel and the sample fluid is in the sample vessel.

In another aspect, a method comprises filling a reference vessel with a reference fluid and filling a sample vessel with a sample fluid. The reference vessel is in fluid communication with a first pressure sensing location of a differential pressure transmitter and the sample vessel in fluid communication with a second pressure sensing location of the differential pressure transmitter. The reference vessel contains the reference fluid in a first column above the first pressure sensing location and the sample vessel contains the sample fluid in a second column above the second pressure sensing location. The second column is of substantially equal height as the first column. The method further comprises measuring, by the differential pressure transmitter, a pressure difference between the first and second pressure sensing locations.

Other objects and features of the present disclosure will be in part apparent and in part pointed out herein.

BRIEF DESCRIPTION OF THE DRAWINGS

Corresponding reference numbers indicate corresponding parts throughout the drawings.

DETAILED DESCRIPTION

Figure 1:
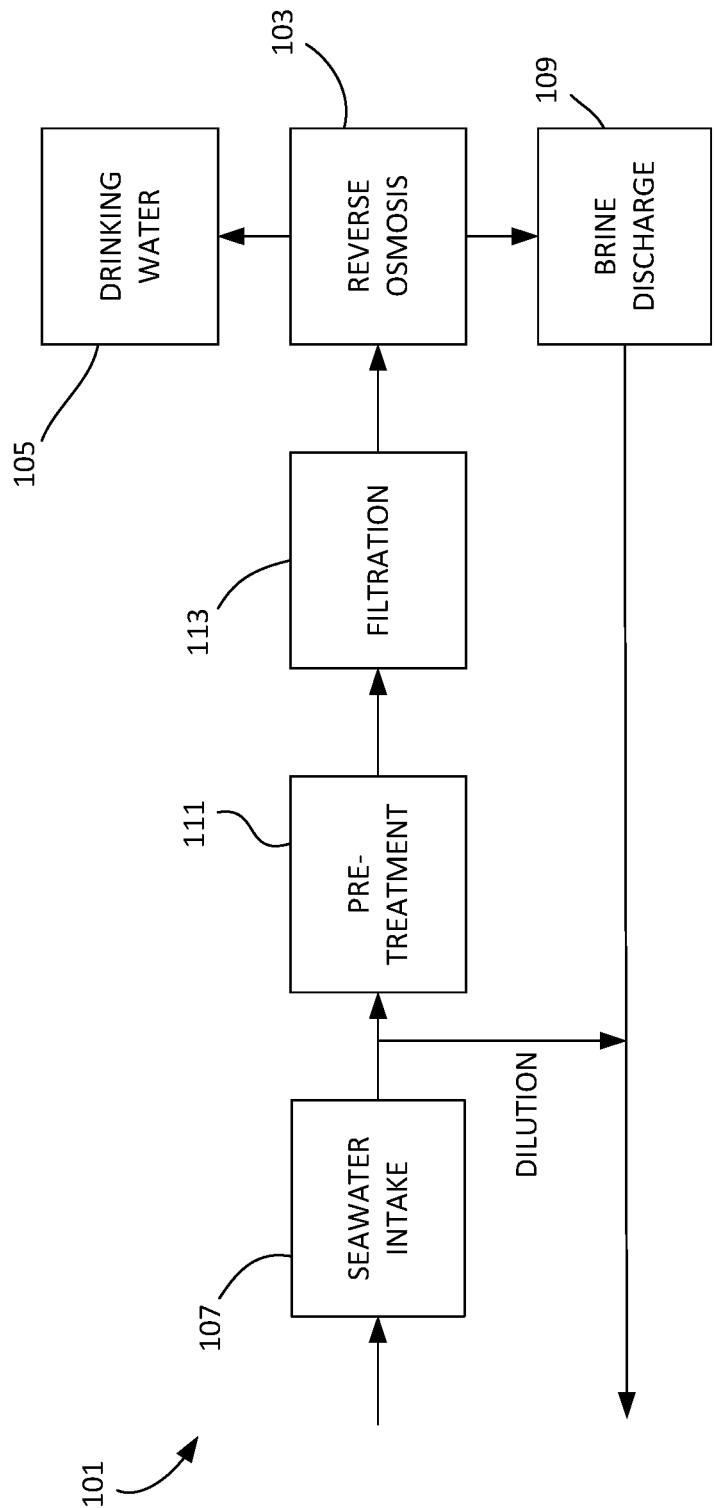
FIG. 1 is a block diagram illustrating a desalination plant according to an embodiment.

FIG. 1 illustrates a conventional desalination plant 101 using a reverse osmosis (RO) process 103 to produce drinking water 105 from seawater 107. The plant 101 separates incoming seawater 107 into the drinking water 105 and concentrated seawater, or brine 109. Before the RO process 103, seawater 107 entering the desalination plant 101 undergoes pre-treatment 111 during which screens remove debris. The pre-treatment 110 also includes, for example, coagulation and flocculation processes in which chemicals are added to seawater 107 to make algae, organic materials, and other particles clump together so they can be removed more easily by filtration 113. The filtration 113 typically includes a sand filter for removing clumped particles followed by a diatomaceous earth (DE) filter to remove silt and finer particles. Typical desalination processes measure total dissolved solids (TDS) in the seawater 107 after filtration 113 and before RO process 103. Cartridge filters may also be employed to remove remaining particles before RO process 103. The RO process 103 involves forcing the pretreated water under high pressure through semi-permeable membranes to separate the freshwater, leaving behind brine 109, which is essentially twice-as-salty seawater with other minerals. After RO process 103, chemicals may be added to stabilize the desalinated seawater, resulting in drinking water 105. The brine 109 is diluted with seawater 107 to lower the overall salinity to nearly match the salinity of the source seawater before being discharged back to the original source. Typical desalination processes measure TDS before the RO process 103 and of the outgoing brine 109.

Figure 2:
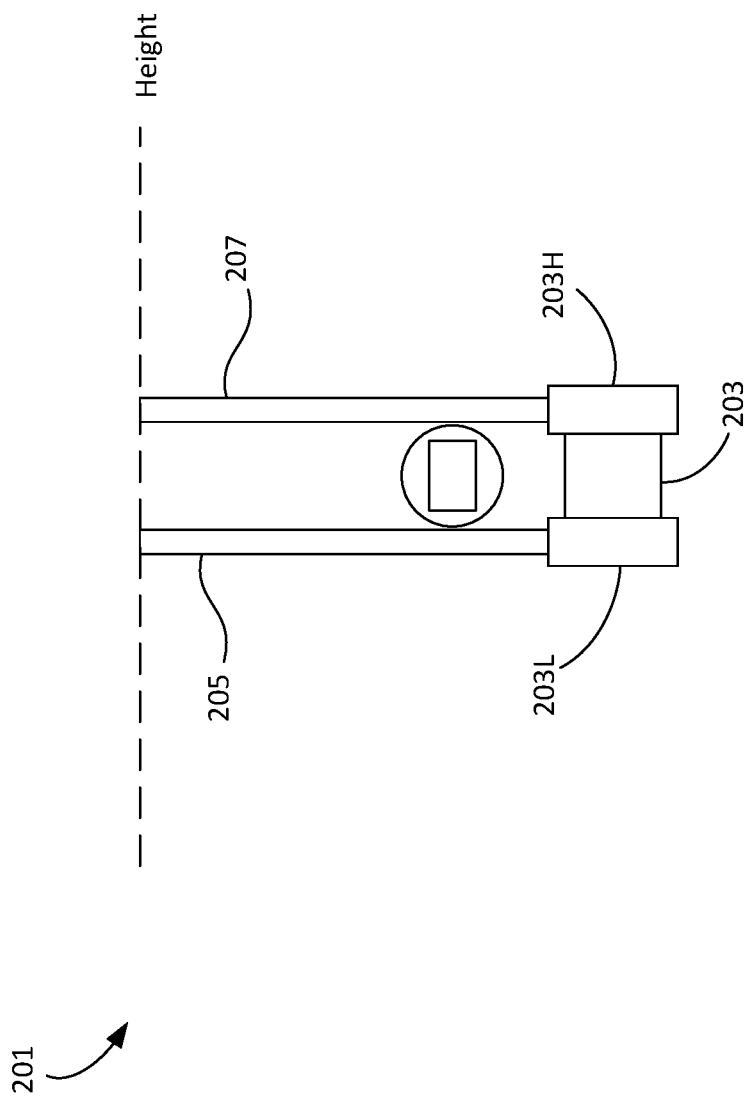
FIG. 2 illustrates a differential density system employing a DP transmitter according to an embodiment.

Referring now to FIG. 2, a system 201 for directly determining TDS using a differential pressure (DP) transmitter 203 is shown. The illustrated system 201 uses a specific measurement configuration along with the DP transmitter 203 to calculate TDS. As described in greater detail below, system 201 provides an accurate value for TDS with minimal temperature affects. This results in a more repeatable TDS value over a desired operating range. Thus, aspects of the present disclosure minimize temperature error on the TDS calculation and provide improved accuracy and repeatability over traditional conductivity-based TDS measurements.

It is to be understood that the system 201 of FIG. 2 produces accurate density measurement that can be applied to other applications (e.g., oil/gas, food) that require accurate density measurements and can be accomplished by a relative density measurement.

The DP transmitter 203 is a device that directly measures the difference between two pressures. This allows the full transmitter resolution and accuracy to be applied to the differential measurement. In this manner, DP transmitter 203 is an improvement over measuring the two pressures independently and subtracting the difference. Measuring the two pressures independently is subject to accuracy and resolution issues for each measurement. In an embodiment, the pressure transmitter 203 comprises a diaphragm and the first pressure sensing location is one side of the diaphragm and the second pressure sensing location is an opposite side of the diaphragm.

Assuming P1 and P2 as a resolution of 1% (1 part in 100), DP as a resolution of 1% (0.01 of 1), and P1 and P2 can read ten times the pressure of DP, the following math would apply

Example 1

Differential pressure=0.58
P1=99, P2=(99+differential pressure of 0.585)
For two pressure measurements,
P1=99, P2=99+0.585 (due to resolution, reported as 100)
Calculated differential pressure=P2−P1=100−99
Resulting error=(1−0.585)/0.585=71% of 0.585
In contrast, for a DP transmitter,
DP has (99.58−99) applied
The difference is directly measured (due to resolution, reported as 0.6)
Resulting error=(0.59−0.58)/0.585=1% of 0.585

Example 2

Differential pressure=0.165
P1=99, P2=(99+differential pressure of 0.165)
For two pressure measurements,
P1=99, P2=99+0.165 (due to resolution, reported as 100)
Calculated differential pressure=P2−P1=100−99
Resulting error=(1−0)/0.165=>100% error or 0.16
In contrast, for a DP transmitter, DP has (99.165−99) applied
The difference is directly measured (due to resolution, reported as 0.17)
Resulting error=(0.17−0.165)/0.165=3% of 0.165

Referring again to FIG. 2, the system 201 directly measures the difference in two fluid densities. Measuring the density difference in two fluids is done by applying a reference fluid in a first vessel coupled to a first pressure sensing location 203L of transmitter 203 (e.g., the low side) and applying an unknown sample fluid in a second vessel coupled to a second pressure sensing location 203H of transmitter 203 (e.g., the high side). In this embodiment, the first vessel is a reference tube, or leg, 205 and the second vessel is a sample tube, or leg, 207. Both legs 205, 207 have the same barometric pressure applied. In an embodiment, the first pressure sensing location may include a low side of the process diaphragm of the pressure transmitter and the second pressure sensing location may include a high side of the process diaphragm of the pressure transmitter. The DP transmitter 203 measures the difference between the pressures exerted by the reference and sample fluids. In the illustrated embodiment, both legs 205, 207 are at equal and known heights above transmitter 203 such that the heights of the two columns of fluids contained therein are also at equal and known heights above transmitter 203. This configuration enables transmitter 203 to measure the difference in pressures exerted by the reference fluid in leg 205 and the sample fluid in leg 207. In turn, the difference in fluid densities can be calculated:

LowSide Pressure=Height*Reference Fluid Density

HighSide Pressure=Height*Sample Fluid Density

TDS=(HighSide Pressure−LowSide Pressure)/Height

The diameters of the legs 205, 207 do not affect the TDS calculation. Only the height of the fluid affects the pressure applied to the high side and low side pressures. The volume could be affected by temperature but this error is removed by ensuring the heights of the columns of fluids are the same. This is accomplished by over filling the legs 205, 207 and allowing the excess to spill out. The temperature of the legs can be used to adjust the leg height due to a temperature change from the reference temperature height. This is accomplished by using the thermal coefficient of expansion of the tubes. This is not critical and only represents a small correction.

For a desalination application, the reference fluid in leg 205 is fresh water or comparable water (e.g., deionized water, distilled water, or the fresh water produced by the desalination process) and the sample fluid in leg 207 is a sample of the water at selected points during the desalination process. The amount of impurities in the reference solution can affect accuracy. The reference water is replaced periodically to minimize potential impurities from being in solution. Assuming incoming seawater 107 is water plus total dissolved solids (TDS) and both fluids are at the same known height, the TDS can be calculated based on the DP measurement from DP transmitter 203. Temperature errors are very small when the two fluids and associated components of system 201 are at the same temperature. Thus, keeping the reference fluid and the sample fluid at the same temperature minimizes any temperature effects.

Example measurement accuracy: Assuming only transmitter measurement accuracy errors, the setup of system 201 calculates a TDS of 45 kg/m$^3$+/−0.1 kg/m$^3$ with a reference fluid of 1000 kg/m$^3$ and a sample fluid of 1045 kg/m$^3$ at 1 meter of height.

Figure 3:
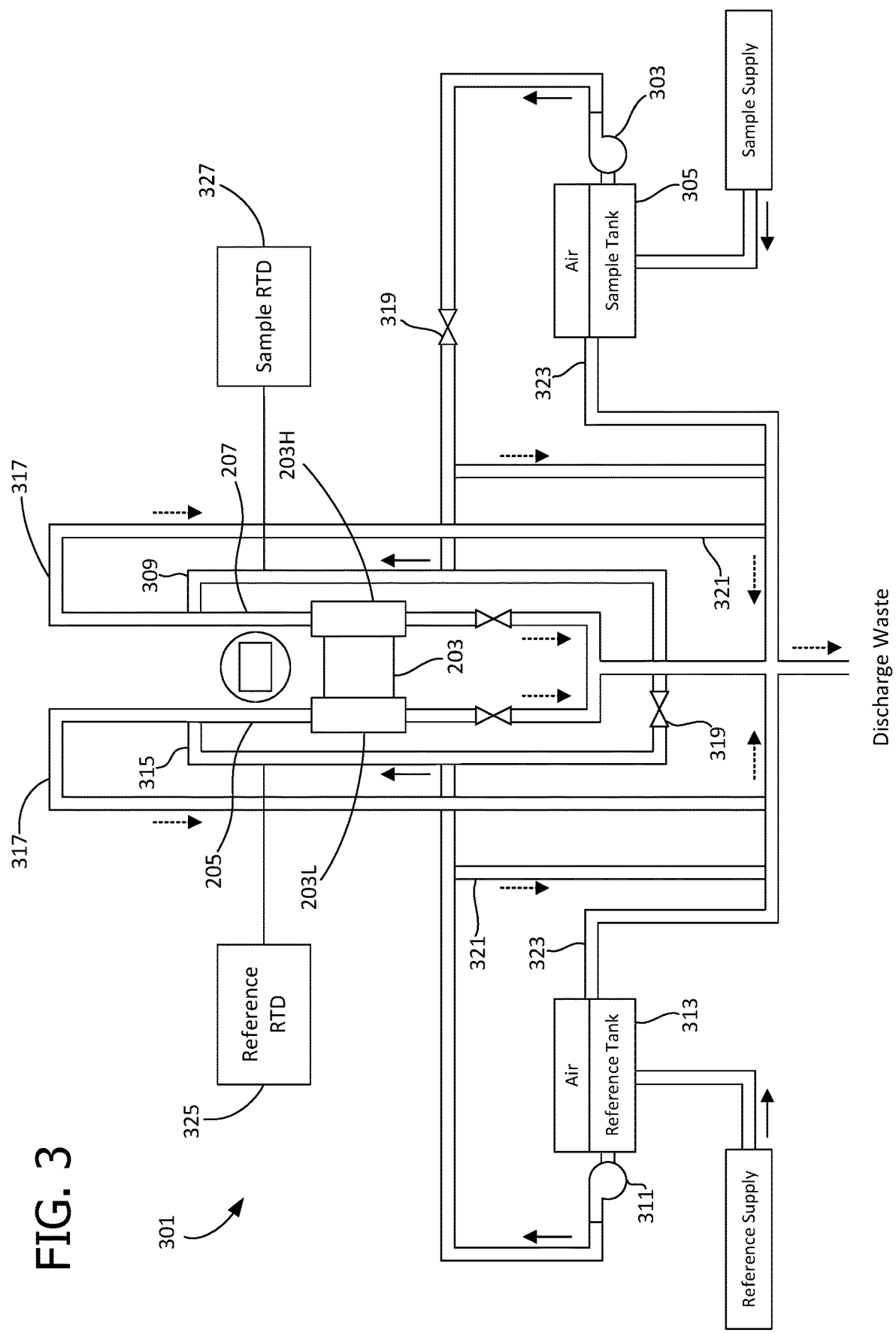
FIGS. 3 to 6 illustrate differential density systems employing DP transmitters according to alternative embodiments.

FIG. 3 illustrates a system 301 embodying aspects of the present disclosure for use in an industrial application. In an industrial application, for instance, the reference and sample fluids are provided to legs 205 and 207, respectively, using a batch process with additional piping. This permits automated TDS measurements. The process fills the reference fluid in communication with the first pressure sensing location 203L of DP transmitter 203 (e.g., low side) via leg 205 and fills the sample fluid in communication with the second pressure sensing location 203H of DP transmitter 203 (e.g., high side) via leg 207. After the fluids have settled, DP transmitter 203 measures the difference in the pressure between the second and first pressure sensing locations (i.e., between 203H and 203L) and calculates the density difference as a function thereof. In this instance, the density difference is the TDS because the fluid heights are the same.

In operation, a pump 303 pumps the sample fluid from a sample reservoir or tank 305 into the leg 207. The sample fluid flows into leg 207 and excess fluid discharges via an overflow pipe 309. Similarly, a pump 311 pumps the reference fluid from a reference reservoir or tank 313 into the leg 205. Excess reference fluid discharges via an overflow pipe 315. The overflow pipes 309, 315 maintain reference leg 205 and sample leg 207 at the same height. In an embodiment, overflow pipes 309, 315 comprise small tubes so that they drain slowly. As shown in FIG. 3, the system 301 incorporates vent tubes 317, preferably having small heads, to allow slowly draining the fluids to the correct height after pumps 303 and 311 are off.

Referring further to FIG. 3, cross over valves 319 permit using the reference fluid to calibrate system 301. A pump drain 321 is located after each tank 305, 313 to prevent cross contamination. Preferably, the drains 321 each have a small diameter to cause slow draining to minimize effects on fluid levels. A tank drain 323 is located on each tank 305, 313 and set at a height to maintain an air space within the tank. As shown, a temperature sensor 325 measures the temperature of the reference fluid in leg 205 and a temperature sensor 327 measures the temperature of the sample fluid in leg 207 for use in making thermal corrections.

Figure 4:
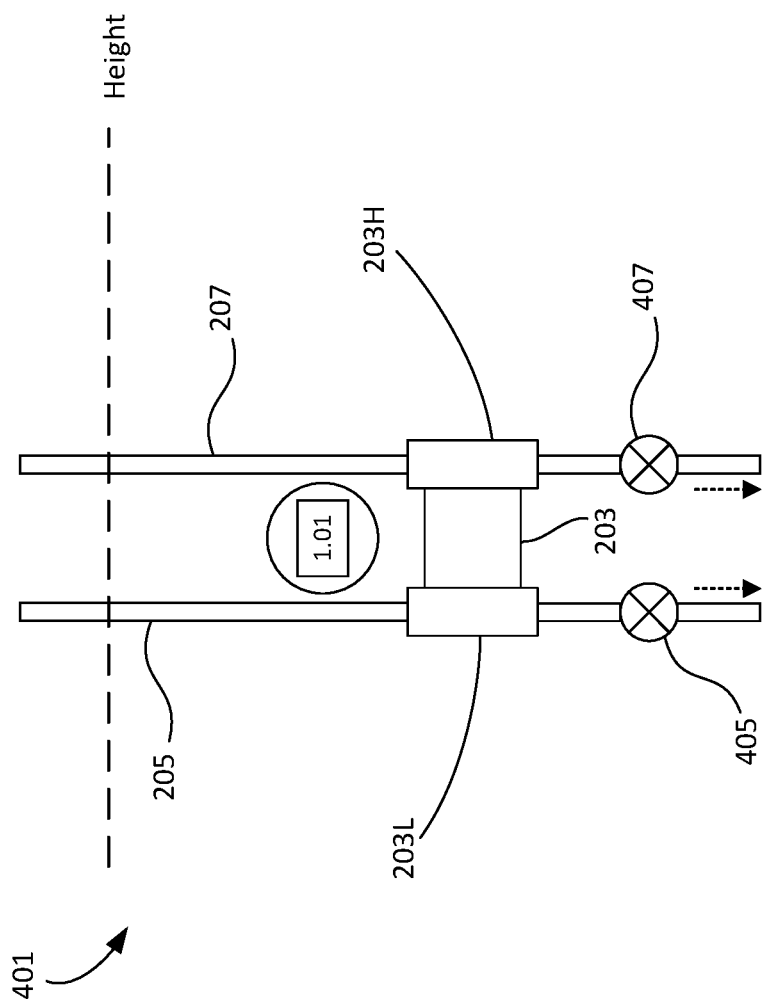

FIG. 4 illustrates a system 401, which is similar to the system 201 with the addition of drain valves 405, 407 to facilitate changing the reference and sample fluids in legs 205 and 207, respectively. In an embodiment, the drain valves 405, 407 are located on downward facing process connections of DP transmitter 203 to permit the fluid to be flush to remove air from the system 401 when changing fluids. It is to be understood that increasing the height of legs 205, 207 improves resolution and reduces error.

In an embodiment, the disclosed DP density measurement systems are self-calibrating by using the same fluid for the reference and for the sample. For example, both legs 205, 207 are filled with the same fluid (e.g., the reference fluid or the sample fluid). Because the fluids are the same, their densities are also the same, and the differential pressure measured by DP transmitter 203 should be zero, assuming equal temperatures and heights. In the event DP transmitter 203 measures a non-zero differential pressure, it is calibrated to zero or an offset is recorded for adjusting the measurement.

In an embodiment, legs 205, 207 are tubes have the same width and height (e.g., an inner diameter of 0.5 inches and a height of 1.5 meters tall). In FIG. 4, for example, the reference leg 205 and the sample leg 207 have overflow drains at the same known height to ensure the fluid columns are the same height. The reference leg 205 and the sample leg 207 also have the same geometry and are made from the same material to minimize thermal errors that could result in the height changing during the measurement. The temperature of the sample fluid is used to set the reference fluid, or vice versa, to the same temperature through use of, for example, a heat exchanger.

Figure 5:
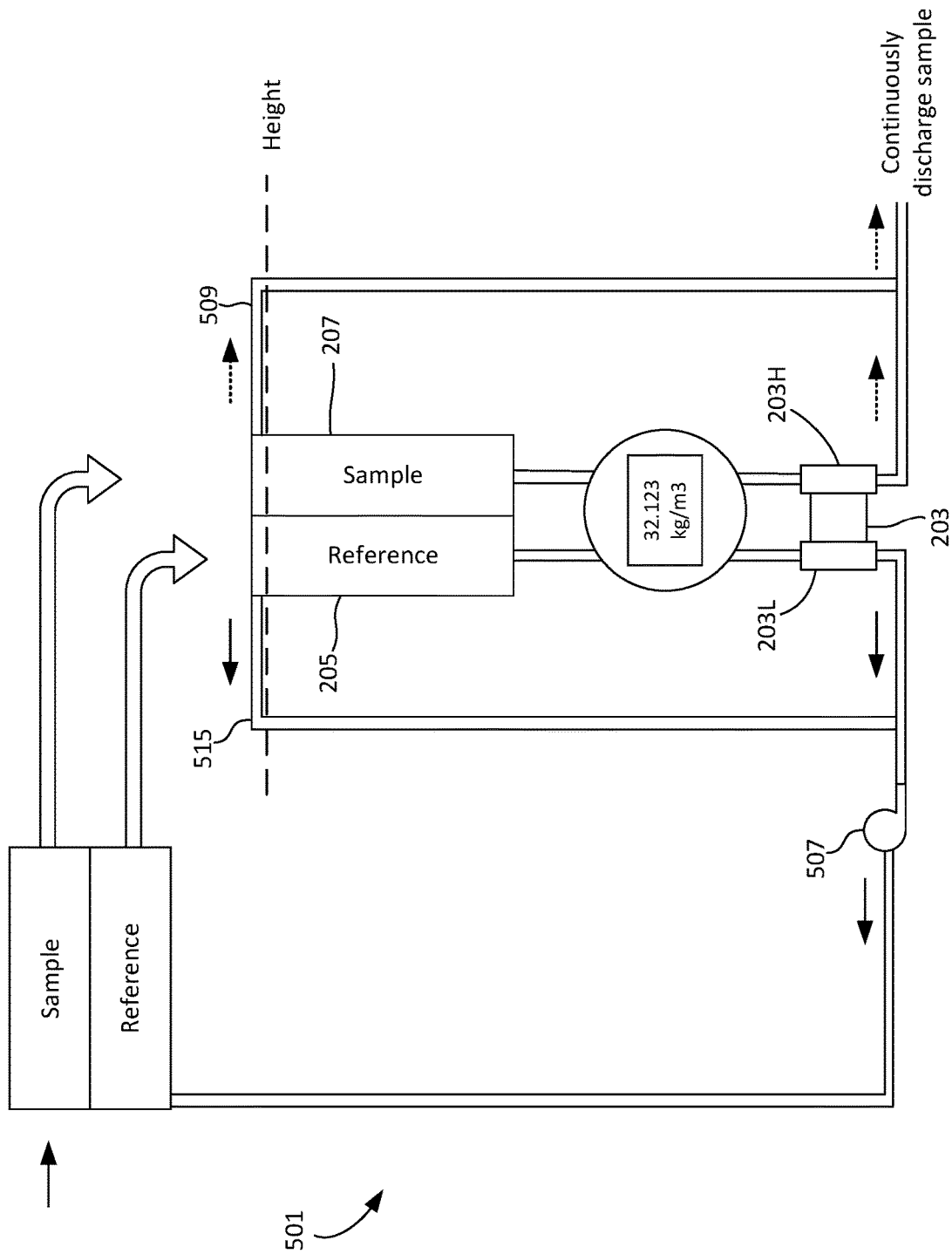

FIG. 5 illustrates a system 501 according to an embodiment including a recirculation pump 507 for periodically circulating the reference fluid. This is done to ensure the temperatures of the sample and reference fluids are the same to minimize fluid thermal expansion errors and to maintain the proper height (e.g., compensate for evaporation). Leveling feet may be used to maintain the overflow points remain consistent and venting both legs ensures the same pressure above the top of the fluids. In this embodiment, the sample fluid is permitted to continually flow into a skid. The calculated value is thus continually available. The reference fluid is recirculated to keep the sample and reference legs 207, 205, respectively, at the same temperature and to replenish any evaporation of the reference fluid. Due to possible variations in height caused by continuous flow, care must be taken to ensure the reference and sample fluids are maintained at the same height. This could include both legs having the same flow rate and having low flow rates. In operation, the sample fluid flows into the open leg 207. The sample fluid flows into leg 207 and excess fluid discharges via an overflow pipe 509. In this embodiment, the reference leg 205 is a closed system. The recirculator pump 507 pumps the reference fluid into leg 205. Excess reference fluid discharges via an overflow pipe 515 where it can be recirculated. The overflow pipes 509, 515 maintain reference leg 205 and sample leg 207 at the same height. As shown in FIG. 5, the sample and reference legs 207, 205 are closely coupled to each other to maintain both at the same temperature. In this embodiment, the sample fluid acts as a heat exchanger to set the reference fluid to the same temperature. By recirculating the reference fluid, system 501 maintains the temperature equal to that of the sample fluid and reduces the effects of evaporation.

Figure 6:
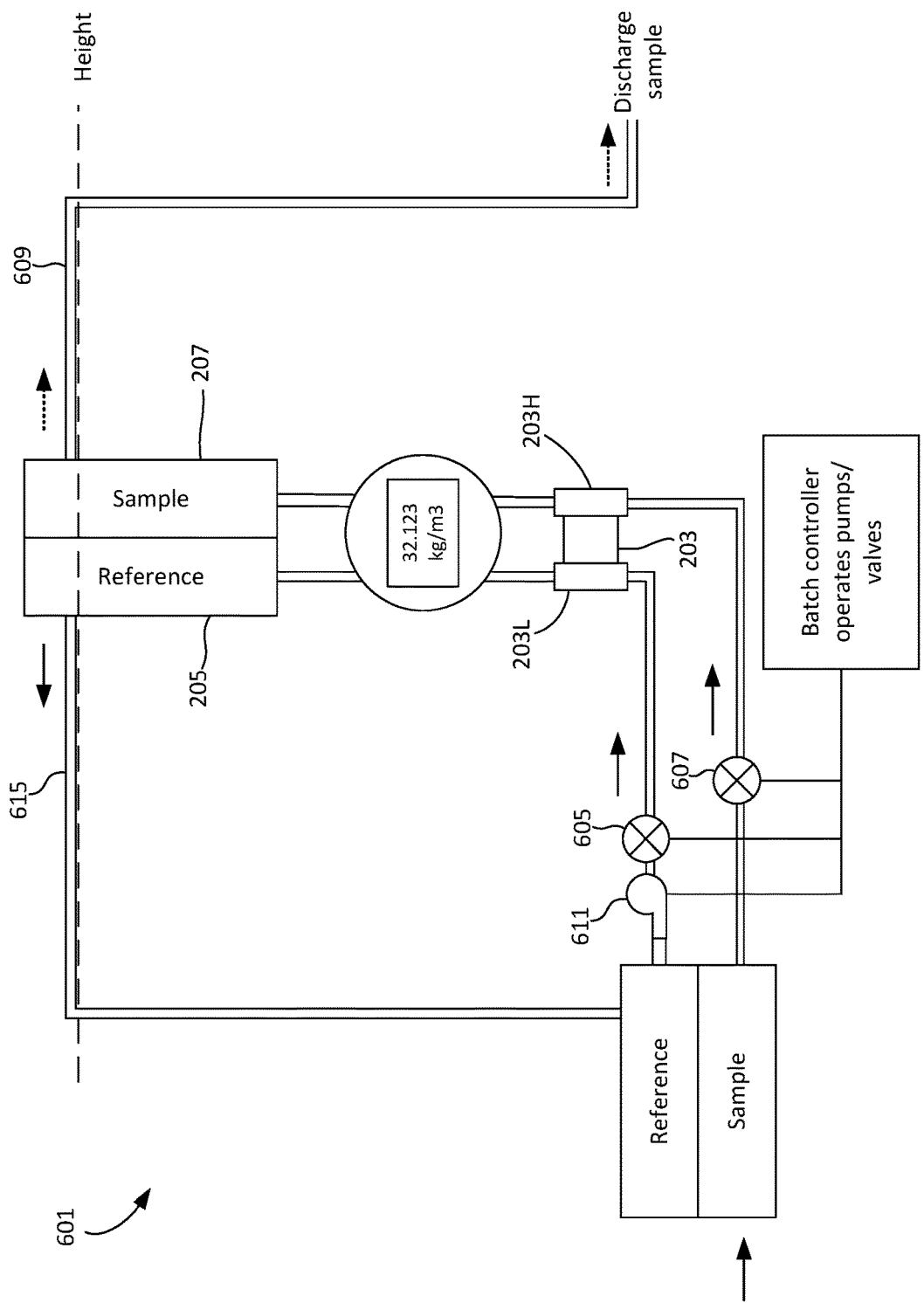

FIG. 6 illustrates a system 601 according to an embodiment for use in a batch process. The data can be renewed on a periodic basis (e.g., every minute). The skid in this embodiment enables valves 605, 607 to empty and refill the current reference and sample legs 205, 207, respectively. The system 601 then waits for a settle time before transmitter 203 makes the differential pressure measurement. Advantageously, trapped air, which affects accuracy, is permitted to escape and the sample fluid is readily replaced. Flushing the reference and sample fluids also flushes sediment that might have collected in the system. In operation, the sample fluid flows into the open leg 207 by way of the valve 607. The sample fluid flows into leg 207 and excess fluid discharges via an overflow pipe 609. In this embodiment, the reference leg 205 is a closed system. A recirculator pump 611 pumps the reference fluid into leg 205 by way of the valve 605. Excess reference fluid discharges via an overflow pipe 615 where it can be recirculated. The overflow pipes 609, 615 maintain reference leg 205 and sample leg 207 at the same height such that the vapor pressure at the top of both legs is equal. As shown in FIG. 6, the sample and reference legs 207, 205 are closely coupled to each other to maintain both at the same temperature. In this embodiment, the sample fluid acts as a heat exchanger to set the reference fluid to the same temperature. By recirculating the reference fluid, system 601 maintains the temperature equal to that of the sample fluid and reduces the effects of evaporation.

Embodiments of the present disclosure may comprise a special purpose computer including a variety of computer hardware, as described in greater detail herein. For instance, the pressure transmitter 203 comprises a processor or other computer hardware that executes processor-executable instructions for calculating a density and/or TDS of the sample fluid based on the differential pressure measurement and the known parameters (i.e., the height of the fluid columns).

For purposes of illustration, programs and other executable program components may be shown as discrete blocks. It is recognized, however, that such programs and components reside at various times in different storage components of a computing device, and are executed by a data processor(s) of the device.

Although described in connection with an example computing system environment, embodiments of the aspects of the invention are operational with other special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the example operating environment. Examples of computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the present disclosure may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the present disclosure may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments may be implemented with processor-executable instructions. The processor-executable instructions may be organized into one or more processor-executable components or modules on a tangible processor readable storage medium. Also, embodiments may be implemented with any number and organization of such components or modules. For example, aspects of the present disclosure are not limited to the specific processor-executable instructions or the specific components or modules illustrated in the figures and described herein. Other embodiments may include different processor-executable instructions or components having more or less functionality than illustrated and described herein.

The order of execution or performance of the operations in accordance with aspects of the present disclosure illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of the invention.

When introducing elements of the invention or embodiments thereof, the articles "a," "an," "the," and "said" are intended to mean that there are one or more of the elements. The terms "comprising," "including," and "having" are intended to be inclusive and mean that there may be additional elements other than the listed elements.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively, or in addition, a component may be implemented by several components.

The above description illustrates embodiments by way of example and not by way of limitation. This description enables one skilled in the art to make and use aspects of the invention, and describes several embodiments, adaptations, variations, alternatives and uses of the aspects of the invention, including what is presently believed to be the best mode of carrying out the aspects of the invention. Additionally, it is to be understood that the aspects of the invention are not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

It will be apparent that modifications and variations are possible without departing from the scope of the invention defined in the appended claims. As various changes could be made in the above constructions and methods without departing from the scope of the invention, it is intended that all matter contained in the above description and shown in the accompanying drawings shall be interpreted as illustrative and not in a limiting sense.

In view of the above, it will be seen that several advantages of the aspects of the invention are achieved and other advantageous results attained.

The Abstract and Summary are provided to help the reader quickly ascertain the nature of the technical disclosure. They are submitted with the understanding that they will not be used to interpret or limit the scope or meaning of the claims. The Summary is provided to introduce a selection of concepts in simplified form that are further described in the Detailed Description. The Summary is not intended to identify key features or essential features of the claimed subject matter, nor is it intended to be used as an aid in determining the claimed subject matter.

The invention claimed is:

1. A differential density system comprising:
a differential pressure transmitter having first and second pressure sensing locations, a reference vessel in fluid communication with the first pressure sensing location, the reference vessel configured to contain a reference fluid in a first column above the first pressure sensing location;
a sample vessel in fluid communication with the second pressure sensing location, the sample vessel configured to contain a sample fluid in a second column above the second pressure sensing location, the second column being of substantially equal height as the first column;
wherein the differential pressure transmitter is configured to measure a pressure difference between the first and second pressure sensing locations when the reference fluid is in the reference vessel and the sample fluid is in the sample vessel; and
a pump for recirculating the reference fluid out of and into the reference vessel.

2. The differential density system as set forth in claim 1, wherein the pressure difference measured by the differential pressure transmitter is proportional to a differential density between the sample fluid and the reference fluid as a function of the height of the first and second columns.

3. The differential density system as set forth in claim 1, wherein a value of total dissolved solids (TDS) in the sample fluid is a function of the pressure difference measured by the differential pressure transmitter and the height of the first and second columns.

4. The differential density system as set forth in claim 1, wherein the reference vessel comprises a first tube and the sample vessel comprises a second tube having substantially identical to the first tube.

5. The differential density system as set forth in claim 1, further comprising a first overflow associated with the reference vessel and a second overflow associated with the sample vessel, the first and second overflows being positioned at substantially the same height relative to the first and second pressure sensing locations to ensure the first and second columns are of substantially equal height.

6. The differential density system as set forth in claim 1, further comprising a first drain valve associated with the first pressure sensing location and a second drain valve associated with the second pressure sensing location, the first drain valve in fluid communication with the reference vessel and the first pressure sensing location and configured for draining the reference fluid therefrom, and the second drain valve in fluid communication with the sample vessel and the second pressure sensing location and configured for draining the sample fluid therefrom.

7. The differential density system as set forth in claim 1, wherein the reference fluid comprises fresh water and the sample fluid comprises seawater.

8. The differential density system as set forth in claim 1, wherein differential pressure transmitter comprises a process diaphragm, and wherein the first pressure sensing location comprises a low side of the process diaphragm of the pressure transmitter and the second pressure sensing location comprises a high side of the process diaphragm of the pressure transmitter.

9. The differential density system as set forth in claim 1, further comprising a first temperature sensor configured for measuring a temperature of the reference fluid and a second temperature sensor configured for measuring a temperature of the sample fluid, wherein the differential pressure transmitter is configured to determine a thermal correction as a function the measured temperatures of the reference fluid and the sample fluid and is further configured to adjust the measured pressure difference as a function of the thermal correction.

10. A method comprising:
filling a reference vessel with a reference fluid, the reference vessel in fluid communication with a first pressure sensing location of a differential pressure transmitter, the reference vessel containing the reference fluid in a first column above the first pressure sensing location;
filling a sample vessel with a sample fluid, the sample vessel in fluid communication with a second pressure sensing location of the differential pressure transmitter, the sample vessel containing the sample fluid in a second column above the second pressure sensing location, the second column being of substantially equal height as the first column;
measuring, by the differential pressure transmitter, a pressure difference between the first and second pressure sensing locations; and
determining a value of total dissolved solids (TDS) in the sample fluid as a function of the pressure difference measured by the differential pressure transmitter and the height of the first and second columns.

11. The method as set forth in claim 10, further comprising filling the reference vessel and the sample vessel with an identical fluid and calibrating the differential pressure transmitter to measure a pressure difference of zero.

12. The method as set forth in claim 10, further comprising calculating a differential density between the sample fluid and the reference fluid as a function of the height of the first and second columns and the pressure difference measured by the differential pressure transmitter.

13. The method as set forth in claim 10, further comprising coupling the reference vessel and the sample vessel closely together such that the reference fluid and the sample fluid have substantially equal temperatures.

14. The method as set forth in claim 10, further comprising:
providing a first drain valve associated with the first pressure sensing location and a second drain valve associated with the second pressure sensing location, the first drain valve in fluid communication with the reference vessel and the first pressure sensing location and the second drain valve in fluid communication with the sample vessel and the second pressure sensing location; and
draining the reference fluid from the reference vessel via the first drain valve and draining the sample fluid from the sample vessel via the second drain valve after measuring the pressure difference between the first and second pressure sensing locations.

15. The method as set forth in claim 10, further comprising measuring a temperature of the reference fluid and measuring a temperature of the sample fluid.

16. The method as set forth in claim 15, further comprising compensating for variations in the height of the reference fluid in the reference vessel based on the temperature of the reference fluid.

17. The method as set forth in claim 15, further comprising compensating for variations in the height of the sample fluid in the sample vessel based on the temperature of the sample fluid.

18. The method as set forth in claim 15, further comprising providing a thermal correction to the measured pressure difference as a function the measured temperatures of the reference fluid and the sample fluid.

19. A method comprising:
filling a reference vessel with a reference fluid, the reference vessel in fluid communication with a first pressure sensing location of a differential pressure transmitter, the reference vessel containing the reference fluid in a first column above the first pressure sensing location;
filling a sample vessel with a sample fluid, the sample vessel in fluid communication with a second pressure sensing location of the differential pressure transmitter, the sample vessel containing the sample fluid in a second column above the second pressure sensing location, the second column being of substantially equal height as the first column;
measuring, by the differential pressure transmitter, a pressure difference between the first and second pressure sensing locations; and
recirculating the reference fluid out of and into the reference vessel.

* * * * *